US009074160B2

(12) United States Patent
Roe et al.

(10) Patent No.: US 9,074,160 B2
(45) Date of Patent: Jul. 7, 2015

(54) PRODUCTION OF OMEGA-3 FATTY ACIDS FROM PYTHIUM SPECIES

(71) Applicant: Algysis LLC, Cleveland, OH (US)

(72) Inventors: Charles L. Roe, Highland Heights, OH (US); James P. Wynn, Lansing, MI (US)

(73) Assignee: AlgiSys, LLC, Cleveland, OH (US)

(*) Notice: Subject to any disclaimer, the term of this patent is extended or adjusted under 35 U.S.C. 154(b) by 121 days.

(21) Appl. No.: 13/788,372

(22) Filed: Mar. 7, 2013

(65) Prior Publication Data

US 2014/0256973 A1 Sep. 11, 2014

(51) Int. Cl.
*A23D 9/00* (2006.01)
*C12P 7/64* (2006.01)
*C11B 1/10* (2006.01)

(52) U.S. Cl.
CPC ............ *C11B 1/10* (2013.01); *C12P 7/6463* (2013.01); *C12P 7/6472* (2013.01)

(58) Field of Classification Search
CPC .... C12P 7/6427; C12P 7/6472; C12P 7/6463; C12P 7/6454; A23D 9/00; C07C 57/03; C07C 69/587; A01H 5/10; A23L 1/3008
USPC .......................................... 554/224; 435/134
See application file for complete search history.

(56) References Cited

U.S. PATENT DOCUMENTS

2001/0025114 A1    9/2001  Bijl et al.
2009/0286292 A1*  11/2009  Wen et al. ............... 435/134
2013/0005004 A1    1/2013  Wen et al.

FOREIGN PATENT DOCUMENTS

WO    WO2012/109563         8/2012
WO    WO 2012109563 A1  *  8/2012

OTHER PUBLICATIONS

International Search Report and the Written Opinion of the International Searching Authority, PCT/US14/19882, Algisys, LLC, Sep. 5, 2014.

* cited by examiner

*Primary Examiner* — Deborah D Carr
(74) *Attorney, Agent, or Firm* — McDonald Hopkins LLC

(57) ABSTRACT

The present invention relates to the production of a triacylglycerol oil that is produced from a *Pythium* species of alga. In one embodiment, the algal species contains at least about 20 weight percent total lipids and contains at least about 10 weight percent of its total fatty acids as eicosapentaenoic acid (EPA) and less than about 5 weight percent of its total fatty acids as arachidonic acid (ARA). In another embodiment, the present invention relates to various methods to produce eicosapentaenoic acid (EPA) from a *Pythium* species of algae. In particular, *Pythium irregulare* can be utilized as a viable production organism.

9 Claims, 1 Drawing Sheet

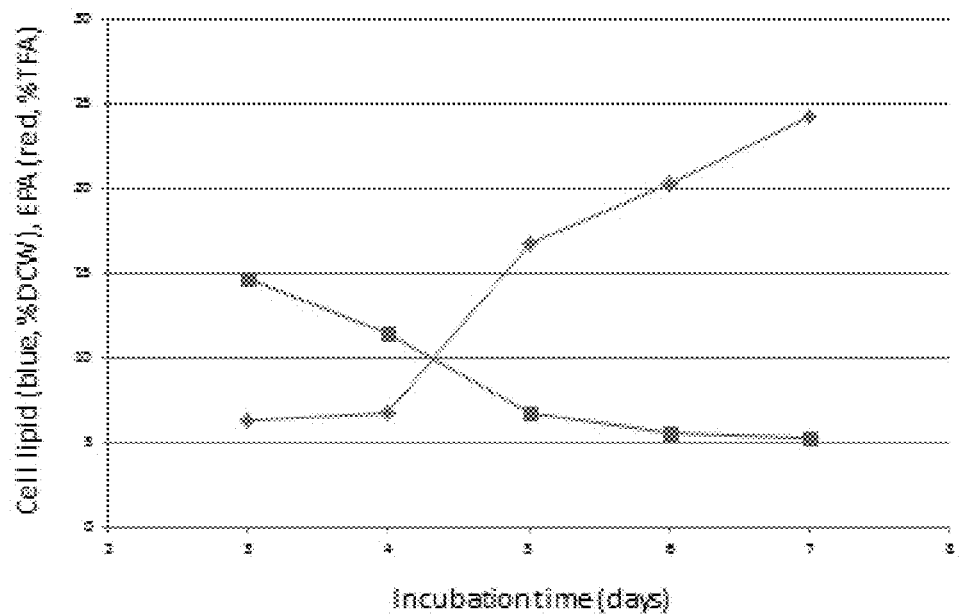

PRODUCTION OF OMEGA-3 FATTY ACIDS FROM PYTHIUM SPECIES

FIELD OF THE INVENTION

The present invention relates to the production of a triacylglycerol oil that is produced from a *Pythium* species of alga. In one embodiment, the algal species contains at least about 20 weight percent total lipids and contains at least about 10 weight percent of its total fatty acids as eicosapentaenoic acid (EPA) and less than about 5 weight percent of its total fatty acids as arachidonic acid (ARA). In another embodiment, the present invention relates to various methods to produce eicosapentaenoic acid (EPA) from a *Pythium* species of algae. In particular, *Pythium irregulare* can be utilized as a viable production organism.

BACKGROUND OF THE INVENTION

Eicosapentaenoic acid (EPA, C20:5, n-3) is an important fatty acid in the omega-3 family based on its medically established therapeutic capabilities against cardiovascular and other diseases. Fish oil as the main source of EPA has several limitations such as undesirable taste and odor, heavy metal contamination, potential shortage due to overfishing, variation in seasonal availability of source fish, and cost of production. Thus, it would be highly beneficial to identify and develop new sources of EPA. The Pythium family of microorganisms contains a number of strains that have the capacity to produce EPA. In particular, *Pythium irregulare* has been investigated extensively as a source for EPA, but no commercial process for production of a high EPA triacylglyerol oil from this source has been developed.

Due to the nutritional benefits of EPA (anti-inflammatory properties etc.) it would be advantageous to be obtain a triacylglycerol oil, from a species of the fungus/alga *Pythium* that contains a high (>10% of total fatty acids) content of EPA. In order to obtain such an oil it would be advantageous if this oil could be extracted from *Pythium* biomass containing high (>20% w/w) of the dry cell weight as lipid.

SUMMARY OF THE INVENTION

The present invention relates to the production of a triacylglycerol oil that is produced from a *Pythium* species of alga. In one embodiment, the algal species contains at least about 20 weight percent total lipids and contains at least about 10 weight percent of its total fatty acids as eicosapentaenoic acid (EPA) and less than about 5 weight percent of its total fatty acids as arachidonic acid (ARA). In another embodiment, the present invention relates to various methods to produce eicosapentaenoic acid (EPA) from a *Pythium* species of algae. In particular, *Pythium irregulare* can be utilized as a viable production organism.

In one embodiment, the present invention relates to a triacylglycerol oil derived from a *Pythium* biomass comprising: greater than 20% w/w dry cell weight cell lipid; and greater than 10% of total fatty acids is EPA.

In another embodiment, the present invention relates to a triacylglycerol oil derived from a *Pythium* biomass comprising: greater than 20% w/w dry cell weight cell lipid; and/or greater than 10% of total fatty acids is eicosapentaenoic acid (EPA), where arachidonic acid (ARA) comprises less than 5% of total fatty acids.

In still another embodiment, the present invention relates to a process of producing at least one triacylglycerol oil, the process comprising the steps of: (i) providing a suitable amount of *Pythium* cultures; (ii) growing a *Pythium* biomass using a substrate from the suitable amount of *Pythium* cultures; (iii) extracting a triacylglycerol oil from the *Pythium* biomass, wherein the triacylglycerol oil comprises greater than 20% w/w dry cell weight cell lipid and greater than 10% of total fatty acids contained in the at least one triacylglycerol oil is eicosapentaenoic acid (EPA).

BRIEF DESCRIPTION OF THE DRAWINGS

FIG. 1 is a graph illustrating one aspect of the problem solved in the present invention, that as cell lipid in *Pythium* increases to greater than 20% dry cell weight (DCW) the EPA in the cell lipid decreases to less than 10% of the total fatty acids. Therefore it was previously impossible to obtain a triacylglycerol oil that contains high (>10% of its total fatty acids) EPA levels from *Pythium* biomass containing economically viable (>20% w/w dry cell weight) quantities of cell lipid.

DETAILED DESCRIPTION OF THE INVENTION

The present invention relates to the production of a triacylglycerol oil that is produced from a *Pythium* species of alga. In one embodiment, the algal species contains at least about 20 weight percent total lipids and contains at least about 10 weight percent of its total fatty acids as eicosapentaenoic acid (EPA) and less than about 5 weight percent of its total fatty acids as arachidonic acid (ARA). In another embodiment, the present invention relates to various methods to produce eicosapentaenoic acid (EPA) from a *Pythium* species of algae. In particular, *Pythium irregulare* can be utilized as a viable production organism.

Those of skill in the art will recognize that *Pythium* organisms were previously classified as fungi but are now known to have evolved separately from fungi, and to be more closely related to brown algae and diatoms. Their current classification is: Kingdom: Chromalveolata; Phylum: Heterokontophyta; Class: Oomycetes; Order: Pythiales; Family: Pythiaceae; Genus: *Pythium*. *Pythium* represent a group of filamentous, unicellular organisms which physically resemble fungi, and are often treated or referred to as such due to their previous classification. Herein, these organisms may be referred to either as algae or fungi, or according to the newer classification as oomycetes. Exemplary species of *Pythium* that may be used in the practice of the invention include, but are not limited, to *Pythium irregulare, Pythium ultimum, Pythium insidiuosum, Pythium debaryanum, Pythium intermedium, Pythium megalacanthum, Pythium paroecandrum*, and *Pythium sylvaticum*. In still another embodiment, when utilized herein the term "*Pythium* species" refers to any *Pythium* species that can be utilized and/or can be genetically or otherwise modified to produce EPA. Accordingly, in one embodiment, the *Pythium* species of the present invention can be a mutant or transformant strain obtained via classical mutation or molecular biology/genetic engineering. In another embodiment, the *Pythium* species used for EPA production is a mutant or transformant of *Pythium irregulare* obtained via classical mutation or molecular biology/genetic engineering.

The preparation of fatty-acid enriched *Pythium* biomass on a commercial scale may be carried out using any suitable industrial equipment, e.g. fermentation tanks or reaction vessels capable of containing volumes of about 10 to 100 m$^3$. Such vessels are generally known to those of skill in the art, and may also comprise, in addition to a means of adding and removing medium, means for, for example, sampling the medium (e.g. to measure pH), means to monitor and adjust the temperature; means to supply gases (e.g. air, oxygen, etc.) to the culture; means to agitate the medium, etc.

In order to begin an industrial scale culture, a substantially pure *Pythium* culture is typically obtained (e.g. a wild type from a strain bank such as the American Type Culture Collection or another suitable source, produced via classic mutation, engineered via molecular biology, etc.) and used to initiate growth of *Pythium* under conditions favorable to spore formation e.g. growth for several (e.g. 3 to 7) days on agar slants typically supplemented with glucose and yeast extract, pH about 5.5 to about 6. To start the serial scale-up liquid cultures, an inoculum of *Pythium* spores is first prepared e.g. by washing the agar surface with distilled water, medium, etc. and the spore solution is added to a bench scale container suitable for large scale growth of the organism. The *Pythium* inoculum contains from about $10^5$ to about $10^7$ spores per liter of culture medium that is inoculated. Then, the culture is "stepped up" gradually by initially inoculating a small volume (e.g. 1 to 2 liters) which is subsequently transferred to successively larger volumes.

During culturing of the *Pythium*, the medium is agitated and air or oxygen (usually air) is supplied to the growing culture. Agitation may be performed, for example, by shaking or rotating the culture (e.g. at an rpm of about 150 to 200 rpm, usually about 170 rpm) in a bench scale flask culture or by a means of agitation or stirring such as paddles, impellors, or another suitable mechanism in a fermentor culture. In a fermentor culture, the fermentor is aerated or oxygenated, usually oxygenated, during growth. Generally, the oxygen concentration is maintained at a level of about 10% to about 80% throughout culturing. Those of skill in the art will recognize that the provision of air or oxygen to the culture may also serve to agitate the culture as the gas is blown into or bubbled through the medium.

Typically, in order to maximize the production of fatty acid-enriched biomass, the culturing of *Pythium* is carried out in two stages. After inoculation of culture medium with the microorganism, a growth phase is undertaken at a temperature of about 20° C. to 30° C. in order to encourage the accumulation of biomass. Generally, the culture is maintained at this temperature range for a period of from about 3 to about 6 days. Thereafter, in order to promote the accumulation of fatty acids in the *Pythium* cells, the temperature is decreased to about 20° C. or below. Culturing continues at lower temperatures for a period of from about 1 to about 3 days. Thus, the total number of days from initial inoculation to harvesting of the *Pythium* biomass is typically from about 5 to about 7 days.

Thereafter, the *Pythium* biomass is harvested by any of several suitable means and methods that are known to those of skill in the art, for example, by centrifugation and/or filtration. Subsequent processing of the biomass is carried out according to its intended use, e.g. by dewatering and drying.

*Pythium* cultured as described herein produces a biomass that is rich is a variety of fatty acids and may be used in a variety of applications. In some embodiments of the invention, the fatty acid enriched biomass that is produced by *Pythium* according to the methods of the invention is used "as is" i.e. the fatty acids are not separated or isolated from the biomass prior to use. In such embodiments, the biomass may be collected and used directly (e.g. as a wet fungal mass) but will more often first be treated by removing some or most or all of the water associated with the biomass. Thus, the invention also encompasses various forms of fully or partially desiccated (dried) biomass produced by *Pythium* that is enriched for fatty acids (e.g. EPA) due to having been cultured as described herein. Such whole dried *Pythium* biomass may be used, e.g. as a food source or additive to feed a variety of organisms, e.g. fish (especially fish grown in aqua cultural fish "farms"); chickens and other poultry (turkeys, Guinea hens, etc.); cows, sheep, goats, horses, and other domestic animals that are typically raised in a "farm" environment (such as dogs, cats, and household pets), etc. The biomass may be used as food for or to supplement the diet of any species that in any way benefits from the intake of fatty acids, especially EPA, to their diet. Of special interest may be the feeding of the biomass to laying hens to increase the quality (type) of the fatty acids in eggs, or to increase the amount of desired fatty acids in eggs. Similarly, the biomass may be fed to animals raised as food in order to increase the quality (type) of the fatty acids in the meat, or to increase the amount of desired fatty acids in meat. Generally, such desired fatty acids include polyunsaturated fatty acids (PUFAs), and in particular, omega-3 fatty acids such as EPA.

In other embodiments of the invention, the fatty acids, especially EPA, may be separated from the biomass, i.e. substantially purified to varying degrees, and then used, e.g. as food supplements or additives. Such fatty acids preparations may contain a mixture of one or more fatty acids originating from the *Pythium* biomass of the invention, or alternatively, the fatty acids may be isolated to provide one or more substantially pure fatty acids.

The biomass and/or fatty acids prepared according to the methods of the invention may be used for purposes other than for food. For example, various skin preparations, cosmetics, soaps, skin cleansers, lotions, sun screen, hair products and other preparations may be formulated to include either the biomass itself, or one or more fatty acids obtained from the biomass. In particular, various "natural" or "green" products may be prepared and marketed as containing biomass that is "naturally" enriched in valuable fatty acids.

As noted above, *Pythium* is a filamentous fungus (alga) that naturally produces eicosapentaenoic acid (20:5, EPA). When the total cell lipid level is low (less than or equal to 10% w/w dry cell weight) the EPA content of the cell lipid is high typically ranging from 12 to 18% of total fatty acids. However when the total cell lipid is low (less than or equal to 10% w/w dry cell weight) the hexane extractable lipid, including triacylglycerols (the commonly used form of lipid in food and nutritional supplements) is very low. It is possible to increase the total amount of cell lipid in *Pythium* to greater than 20% (w/w dry cell weight) lipid by altering the cultivation conditions. Under these conditions the triacylglycerol content of the cells is high and could economically be extracted (e.g. with hexane or another solvent) to produce a triacylglycerol rich oil suitable for use as a food ingredient or nutritional supplement. However when the cell lipid level in *Pythium* is high (e.g., at least about 20 percent w/w of the cell dry weight) the level of EPA decreases to low levels (less than 10% of total fatty acids), as exemplified in FIG. 1. For use as an EPA-rich tricylglycerol oil suitable for food ingredient or nutritional supplement use the EPA content of the oil should preferably be greater than 10%. It should be noted that higher levels of arachidonic acid (e.g. greater than 5% of total cell lipid levels) can also accompany certain *Pythium* strains. Arachidonic acid (ARA) is a polyunsaturated omega-6 fatty acid 20:4(Ω-6) that is a key inflammatory intermediate and can also act as a vasodilator. ARA is therefore often considered an undesirable fatty acid for adult human and animal consumption.

Thus, in one embodiment, the present invention directed to a triacylglycerol oil derived from *Pythium* cells that contains greater than 20% (w/w dry cell weight) cell lipid that is rich in EPA (greater than 10% total fatty acids).

This invention solves the problem of allowing a nutritional triacylglycerol oil rich in EPA and essentially free of DHA to be extracted from cells of the *Pythium* fungus/alga. While others have grown *Pythium* to accumulate high levels of cell lipid, none have succeeded in obtaining a tracylglycerol oil containing a high EPA level (greater than 10% total fatty acids) from *Pythium*, biomass containing >20% w/w of the dry cell weight as cell lipid.

The cells of *Pythium* are cultured under conditions (decreased growth temperature) that permit appreciable cell growth (as measured by final cell dry weight) and lipid accumulation (as measured by total cell lipid) while inducing the cells to accumulate a cell lipid containing high levels of EPA (greater than 10% total fatty acids). This oil also contained very low levels of arachidonic acid (ARA).

In one non-limiting example, a 50 mL of culture medium generates greater than 10 g/L dry cell weight, and produces a *Pythium* biomass containing greater than 25% w/w lipid and the lipid containing greater than 10% EPA (of total fatty acids).

FIG. 1 attached hereto details that as cell lipid increases to greater than 20% dry cell weight (DCW) the EPA in cell lipid decreases to less than 10% of the total fatty acids.

Table 1 below shows that according to the present invention a biomass can be obtained that contains greater than 25% cell lipid and with greater than 10% EPA in that cell lipid. This is the biomass from which the EPA-rich triacylglycerol oil can be obtained.

TABLE 1

|  | Flask 1 | Flask 2 | Typical 25° C. Flask |
|---|---|---|---|
| Cell Lipid (% DCW) | 35.98 | 36.84 | 29.83 |
| Fatty Acid | Percentage of Total Fatty Acids (% TFA) | | |
| 14:0 | 10.73 | 9.97 | 6.93 |
| 16:0 | — | — | — |
| 16:1 | 25.90 | 24.03 | 31.06 |
| 18:0 | — | — | — |
| 18:1 | 24.57 | 22.86 | 27.63 |
| 18:2 | 10.19 | 9.38 | 10.37 |
| 18:3(n-6) | — | — | — |
| 20:3/20:4 | 6.78 | 7.47 | 6.70 |
| 20:4(n-6) ARA | 2.25 | 2.65 | 3.27 |
| 20:5(n-3) EPA | 11.87 | 13.92 | 6.38 |
| EPA/ARA | 5.28 | 5.25 | 1.95 |

Given the above, in one embodiment the present invention makes it possible to produce a triacylglycerol oil derived from a *Pythium*-containing biomass comprising: greater than 20% w/w dry cell weight cell lipid; in which greater than 10% of total fatty acids are eicosapentaenoic acid (EPA). In another embodiment, the present invention relates to a triacylglycerol oil derived from a *Pythium* biomass comprising: greater than 20% w/w dry cell weight cell lipid; in which greater than 10% of total fatty acids is eicosapentaenoic acid (EPA), and wherein arachidonic acid (ARA) comprises less than 5% of total fatty acids. Thus, in some embodiments the present invention permits the production of a triacylglycerol oil with an unique lipid and/or fatty acid content while simultaneously yielding a triacylglycerol oil that contains a lower amount of ARA.

In still another embodiment, the present invention relates to a process of producing at least one triacylglycerol oil using a fermentation step as a method to achieve via a feedstock selected from glycerol (crude or refined), glucose/dextrose, lactose, xylose, sucrose, fructose, or any suitable combination of two or more thereof. In still another embodiment, the present invention relates to a process of producing at least one triacylglycerol oil using a suitable culture medium that comprises a suitable nitrogen source such as yeast extract, DAP, urea, $NaNO_3$, CSL, etc. containing sufficient amounts of nitrogen conducive to growing biomass at concentrations of at least 30 grams per liter.

EXAMPLE

The following example is to be broadly construed and is non-limiting in nature.

Cultivation of the Lipid-Rich Biomass

*Pythium irregulare* ATCC 10951 is cultivated in 250 mL Erlenmeyer flasks containing 50 mL of M#1 (YE) medium. The culture medium contains 30 g/L glucose, 3.0 g/L yeast extract, 7.0 g/L $KH_2PO_4$, 1.5 g/L $MgSO_4.7H_2O$, 0.1 g/L $CaCl_2.2H_2O$, 1.0 g/L NaCl, 4.8 mg/L $FeCl_3$, 1 mg/L $ZnSO_4.7H_2O$, 0.1 mg/L $CoCl_2.6H_2O$, 0.1 mg/L $CuCl_2.2H_2O$, and 0.1 mg/L $MnSO_4.H_2O$. The shake flasks are inoculated with 1 mL of a hyphal suspension produced by vortexing a 1.5 cm×1.5 cm section of an M#1 (YE) agar plate [M#1 (YE) with 20 g/L agar] containing a lawn of *P. irregulare* in a sterile tube with 10 mL of sterile distilled water and approximately twenty 5 mm diameter sterile glass balls.

The shake flasks are incubated (without agitation) for 4 to 8 weeks at 5° C. The biomass is harvested by centrigugation at 15000×g for 5 min and the supernatant is immediately removed. The biomass is washed with 40 mL of distilled $H_2O$ and then freeze dried.

Extraction of the High-EPA Containing Oil

The freeze dried biomass is ground in a pestle and mortar to form a fine powder. The powder is placed in a pre-weighed Erlenmeyer flask and the mass of biomass determined gravimetrically. Five milliliters of hexane per gram of dry biomass is added to the dry biomass and the biomass/hexane slurry is then agitated periodically and incubated at lab temperature for at least 16 hours. The biomass is removed from the hexane extract (micella) by filtration, under gravity through a Whatman No. 1 filter paper and washed with a further 2 mL hexane per gram of dry biomass. The micella is reduced to dryness in a rotavap and the triacylglycerol (TAG) re-dissolved in ethyl acetate. The TAG solution is filtered through a glass wool filter (glass wool packed into a glass pipette) into a pre-weighed tube. The ethyl acetate is removed under a stream of $N_2$ and the amount of TAG extracted determined gravimetrically.

Lipid Analysis

A sample (about 20 mg) of the extracted TAG is taken and esterified using a reaction mixture containing 2 mL MeOH, and 0.15 mL acetylchloride. The reaction mixture is heated to 55° C. for 4 hours and then cooled. The fatty acid methyl ester (FAME) preparation is neutralized with dry $Na_2CO_3$ and filtered through a 0.45 μm nylon filter. The filtrate is used for GC analysis.

The fatty acid profile is determined using GC analysis using a Zebrum ZB Wax column (30 m long with a 0.25 mm diameter). The initial oven temperature is 160° C. and is ramped up to 250° C. at 10° C./min. The column is then held at 250° C. for 9 minutes. The injector and detector temperature is 250° C. The FAMEs are detected using a flame ionization detector and identified based on retention time and comparison with authentic standards.

While in accordance with the patent statutes the best mode and certain embodiments of the invention have been set forth, the scope of the invention is not limited thereto, but rather by the scope of the attached. As such, other variants within the spirit and scope of this invention are possible and will present themselves to those skilled in the art.

What is claimed is:

1. A triacylglycerol oil derived from a *Pythium* biomass comprising:
   greater than 20% w/w dry cell weight cell lipid; and
   greater than 10% of total fatty acids is eicosapentaenoic acid (EPA).

2. The triacylglycerol oil of claim 1, wherein the substrate utilized for growing the *Pythium* biomass is selected from glucose, dextrose, lactose, xylose, sucrose, fructose, or any suitable combination of two thereof.

3. The triacylglycerol oil of claim 1, wherein the biomass further comprises at least one nitrogen source and the nitrogen source is selected from yeast extract, DAP, urea, $NaNO_3$, CSL, or combinations of two or more thereof.

4. A triacylglycerol oil derived from a *Pythium* biomass comprising:
   greater than 20% w/w dry cell weight cell lipid; and
   greater than 10% of total fatty acids is eicosapentaenoic acid (EPA), where arachidonic acid (ARA) comprises less than 5% of total fatty acids.

5. The triacylglycerol oil of claim 4, wherein the substrate utilized for growing the *Pythium* biomass is selected from glucose, dextrose, lactose, xylose, sucrose, fructose, or any suitable combination of two thereof.

6. The triacylglycerol oil of claim 4, wherein the biomass further comprises at least one nitrogen source and the nitrogen source is selected from yeast extract, DAP, urea, $NaNO_3$, CSL, or combinations of two or more thereof.

7. A process of producing at least one triacylglycerol oil, the process comprising the steps of:
   (i) providing a suitable amount of *Pythium* cultures;
   (ii) growing a *Pythium* biomass using a substrate from the suitable amount of *Pythium* cultures;
   (iii) extracting a triacylglycerol oil from the *Pythium* biomass,
   wherein the at least the triacylglycerol oil comprises greater than 20% w/w dry cell weight cell lipid and greater than 10% of total fatty acids contained in the at least one triacylglycerol oil is eicosapentaenoic acid (EPA).

8. The method of claim 7, wherein the substrate utilized for growing the *Pythium* biomass is selected from glucose, dextrose, lactose, xylose, sucrose, fructose, or any suitable combination of two thereof.

9. The triacylglycerol oil of claim 7, wherein the biomass further comprises at least one nitrogen source and the nitrogen source is selected from yeast extract, DAP, urea, $NaNO_3$, CSL, or combinations of two or more thereof.

* * * * *